(12) United States Patent
Basile et al.

(10) Patent No.: US 6,327,912 B2
(45) Date of Patent: Dec. 11, 2001

(54) METHOD FOR MEASURING BY ULTRA-SOUND THE RESIDUAL TENSION OF A PRE-STRESSED BAR

(75) Inventors: Bernard Basile, Plaisir; Bruno Lancia, Marseille, both of (FR)

(73) Assignee: Freyssinet International (STUP) (FR)

( * ) Notice: Subject to any disclaimer, the term of this patent is extended or adjusted under 35 U.S.C. 154(b) by 0 days.

(21) Appl. No.: 09/725,747

(22) Filed: Nov. 29, 2000

(30) Foreign Application Priority Data

Nov. 29, 1999 (FR) .................................................. 99 14989

(51) Int. Cl.[7] ...................................................... F16B 31/02
(52) U.S. Cl. ................................................. 73/761; 73/597
(58) Field of Search .............................. 73/597, 761, 789, 73/826, 581, 602, 627, 631, 629, 799, 801

(56) References Cited

U.S. PATENT DOCUMENTS

| | | | |
|---|---|---|---|
| 4,333,351 | * 6/1982 | Bickford | 73/761 |
| 4,413,518 | 11/1983 | Jones | 73/615 |
| 4,485,677 | * 12/1984 | Amelot et al. | 73/761 |
| 4,899,591 | * 2/1990 | Kibblewhite | 73/761 |
| 5,220,839 | * 6/1993 | Kibblewhite | 73/761 |
| 5,461,923 | * 10/1995 | Meisterling | 73/761 |

FOREIGN PATENT DOCUMENTS

| | | |
|---|---|---|
| 2 507 232 | 12/1982 | (FR) . |
| 2 750 498 | 1/1998 | (FR) . |
| WO 97/11343 | 3/1997 | (WO) . |

* cited by examiner

Primary Examiner—Daniel S. Larkin
Assistant Examiner—Jacques M. Saint-Surin
(74) Attorney, Agent, or Firm—Cantor Colburn LLP

(57) ABSTRACT

In order to measure in situ the residual tension $F_1$ of a pre-stressed bar braced between two anchorages, the two-way propagation time $T_1$ of an ultra-sonic wave between the two ends of the bar is measured, and $F_1$ is evaluated by the formula $F_1 = F_0 + k_b \cdot (T_1 - T_0)$. During a preliminary calibration carried out without demounting, the bar is subjected to a variable traction effort F. For each value, the two-way propagation time T of an ultra-sonic wave between the two ends of the bar is measured, a curve associating the effort F with the time T is recorded, and the constant $T_0$ is determined as being the two-way propagation time measured for F=0, the curve is approached in the neighborhood of the value F=0 by a first straight line of slope $k_a$, an upper portion of the curve is approached by a second straight line of slope $k_L$, the constant $F_0$ is determined as being the traction effort F corresponding to the point of intersection of the first and second straight lines, and the constant $k_b$ is determined according to the relationship $1/k_b = (1/k_L) - (1/k_a)$.

4 Claims, 1 Drawing Sheet

METHOD FOR MEASURING BY ULTRA-SOUND THE RESIDUAL TENSION OF A PRE-STRESSED BAR

BACKGROUND OF THE INVENTION

1. Field of the Invention

The present invention relates to a method for measuring in situ the residual tension $F_1$ of a pre-stressed bar braced between two anchorages, by determining the two-way propagation time $T_1$ of an ultra-sonic wave between the two longitudinal ends of the bar and by evaluating the residual tension $F_1$ by a formula of the form $F_1 = F_0 + k_b \cdot (T_1 - T_0)$ where $F_0$, $T_0$ and $k_b$ are constants determined during a preliminary calibration carried out without demounting the bar.

2. Description of Related Art

A process of this type is described in the French patent 2 750 498. According to this patent, the preliminary calibration consists in:

applying to one end of the pre-stressed bar a traction effort F which progressively increases;

measuring simultaneously the longitudinal displacement A of the end of the pre-stressed bar as well as the above-mentioned traction effort whereby these measurements correspond to a curve of the traction effort F as a function of the displacement A which presents an initial portion substantially following a first straight line having a high slope, then a curved portion and finally a final portion substantially following a second straight line having a lower slope;

determining the residual tension as being the value of the traction effort F which corresponds to the intersection of the two straight lines;

applying successively to the pre-stressed bar at least two known and distinct tension values higher than the residual tension, by traction on the end of said pre-stressed bar;

measuring for each of these tension values the two-way propagation time of an ultra-sonic wave between the two longitudinal ends of the pre-stressed bar;

and deducing from these measurements the constants of the evaluation formula of the residual tension.

Owing to these measures, it is necessary to apply traction efforts to the end of the pre-stressed bar only during calibration, which is carried out once for all.

Once the calibration has been carried out, one can subsequently check as often as necessary the residual tension of the pre-stressed bar solely by measuring the two-way propagation time of an ultra-sonic wave between the two ends of this bar. These subsequent checks are therefore very simple and very quick. This process is well adapted to cases where there are restrictions to the access to the structure, for example due to ionising rays.

An object of the present invention is to improve the accuracy of the processes for measuring residual tension by ultra-sound.

SUMMARY OF THE INVENTION

In a method according to the invention, of the type set out in the introduction, the preliminary calibration comprises the steps of:

subjecting the bar to different values of a traction effort F, applied in a zone situated outside of the interval between the two anchorages;

for each value of the applied traction effort F, measuring the two-way propagation time T of an ultra-sonic wave between the two longitudinal ends of the bar, in such a way as to memorize points of a curve associating the traction effort F with the two-way propagation time T;

determining the constant $T_0$ as being the two-way propagation time T measured for a traction effort F=0;

approaching said curve, in the neighborhood of the traction effort value F=0, by a first straight line having a slope $k_a$;

approaching an upper portion of said curve by a second straight line of inclination $k_L$;

determining the constant $F_0$ as being the traction effort F corresponding to the point of intersection of said first and second straight lines; and determining the constant $k_b$ according to the equation $1/k_b = (1/k_L) - (1/k_a)$.

This enables in particular an improvement in the determination of the coefficient $k_b$, by rigorously taking into account parasite effects that the calibration system can induce. The first straight line approaching the curve (T, F) in the neighborhood of the point ($T_0$, 0) takes into account the elongation of the bar in the region situated between the point of application of the traction effort F and the adjacent anchorage, whereas the second straight line takes into account the increase of the length L between the point of application of the traction effort and the opposite anchorage. In service, and in particular during subsequent verifications, it is only the length b=L−a between the two anchorages which is subjected to the residual tension $F_1$. It is thus judicious for the slope coefficient $k_b$ to be corrected in relation to the slope $k_L$ of the second straight line. This correction will be all the more important if the pre-stressed bar is relatively short.

In a preferred embodiment of the method, the approximation of said curve in the neighborhood of the traction effort value F=0 by a first straight line of slope $k_a$ comprises a fit of a parabola on a lower portion of the curve, and the determination of the first straight line as being the tangent of said parabola for the traction effort value F=0.

In an advantageous embodiment, the preliminary calibration involves a measurement of the temperature of the material of the bar and a memorization of the temperature measured. This enables the temperature effects upon the measured propagation times to be subsequently taken into consideration. Thus, during a measuring phase subsequent to the calibration, the temperature of the material of the bar and the two-way propagation time of an ultra-sonic wave between the two longitudinal ends of the bar are measured, and the time $T_1$ for the application of the above-mentioned formula is determined by correcting the measured two-way propagation time as a function of the deviation between the temperatures measured at the time of the preliminary calibration and the subsequent measuring phase.

DESCRIPTION OF PREFERRED EMBODIMENTS

Figure 1:
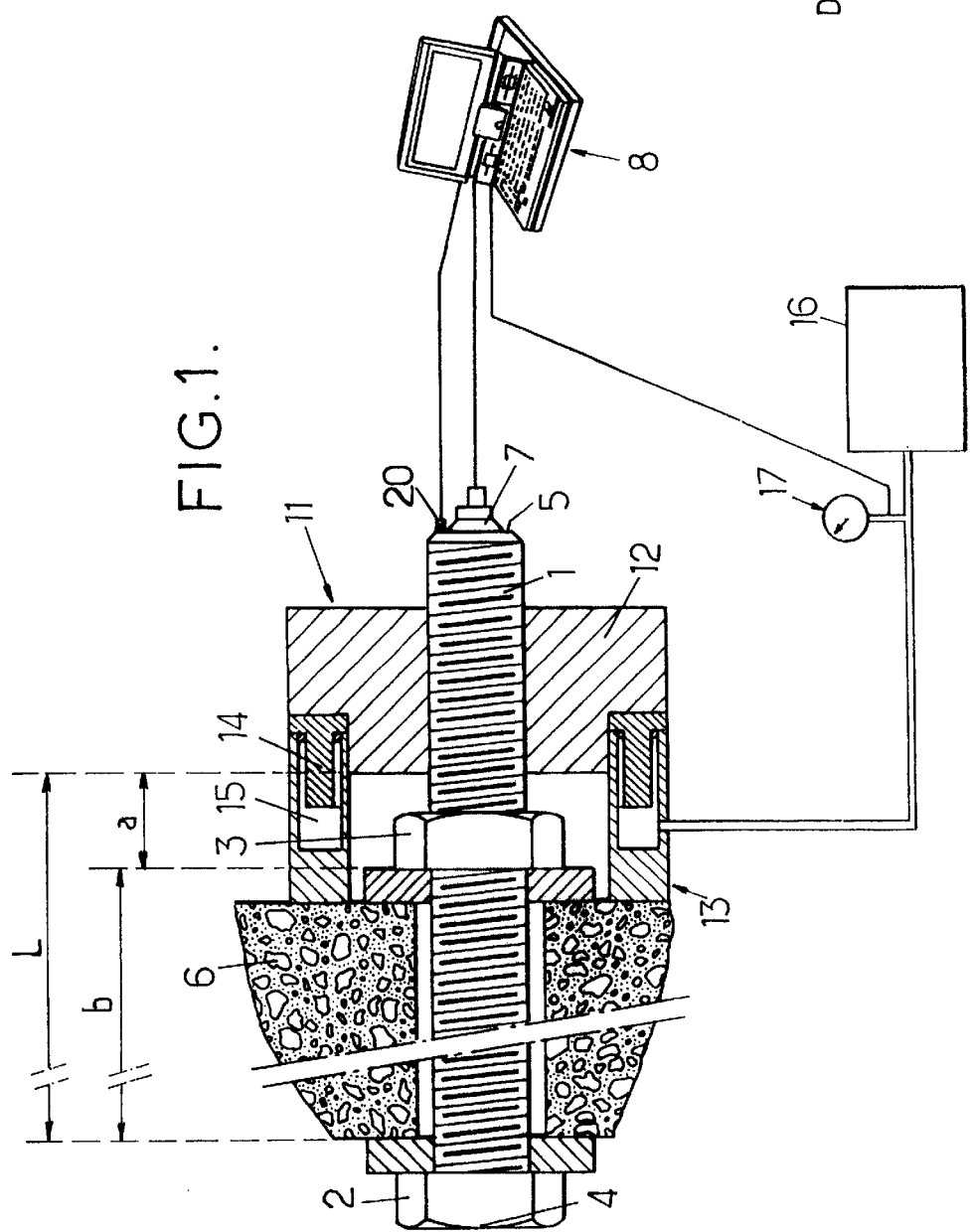
FIG. 1 is a schematic view showing an example of implementation of the method according to the invention.

As is shown in FIG. 1, the process according to the invention is designed to measure the residual tension $F_1$ of a pre-stressed bar 1, for example metallic, which is braced between two anchorages 2, 3 situated respectively in the neighborhood of the longitudinal ends 4, 5 of said bar.

The length of the pre-stressed bar 1 between its two ends 4, 5 is typically less than 5 meter(s) and generally less than 2 meter(s), for example in the range between 50 cm and 2 meter(s).

In the non-limiting example represented in the drawings, the anchorages 2, 3 are constituted as follows: one of them by an enlarged head 2 integral with the pre-stressed bar and the other one by a nut 3 screwed on the bar 1 which is threaded completely or partially. These two anchorages apply a compression effort on a mass of concrete 6 or another mass to be pre-stressed.

In order to be able to regularly check the residual tension $F_1$ of the pre-stressed bar 1 by ultra-sound, a preliminary calibration of the device relatively to the bar under consideration is undertaken.

For this purpose, the bar 1 is equipped outside the mass 6 with an ultra-sonic transducer 7 and with a unit 11 enabling a traction to be exerted on the pre-stressed bar.

The transducer 7, for transmitting and sensing ultra-sonic waves, is placed on the end 5 of the bar 1. It is linked directly or indirectly to a special electronic card integrated in a micro-computer 8, whereby this card enables the transducer 7 to be controlled in order to emit to the end 5 an ultra-sonic wave, preferably as a pulse.

The transducer 7 also permits to sense the echo of this wave at the end 5 after reflection on the end 4 of the pre-stressed bar, in order to measure the two-way propagation time T of the ultra-sonic wave between the two ends.

In the example represented in FIG. 1, the unit 11 has a metal ring 12 screwed on a zone of the pre-stressed bar 1 situated between its end 5 and the anchorage 3, and an annular hydraulic jack 13 positioned around the pre-stressed bar 1 and interposed axially between the mass 6 and the ring 12, whereby this jack has an annular piston 14 which slides in an annular cylinder 15 supplied with hydraulic fluid by a pump 16.

The hydraulic circuit of the jack 13 is equipped with a pressure sensor 17 to measure the traction force exerted by the jack 13 on the pre-stressed bar 1 (taking into consideration the useful section of the jack and its yield). Alternatively, the measurement of the effort could be carried out by placing a strain gauge between the jack 13 and the ring 12, or between the mass 6 and the jack 13.

The effort measured is sent to an electronic acquisition card belonging to the micro-computer 8 in such a way that this micro-computer can record the value of the traction efforts F applied to the pre-stressed bar 1.

During the calibration stage, the pump 16 is controlled in order to progressively increase the traction effort F applied to the pre-stressed bar, and during this time the micro-computer 8 measures and records simultaneously the two-way propagation time T by means of the transducer 7 placed at the end 5 of the pre-stressed bar and the traction effort F by means of the sensor.

Figure 2:
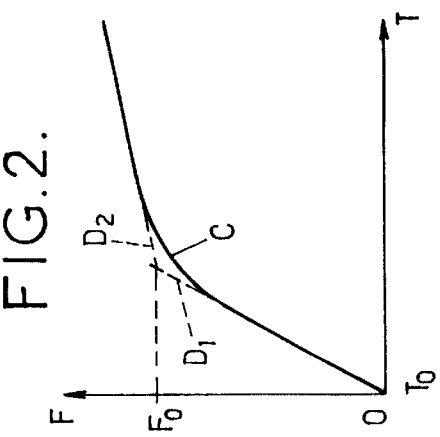
FIGS. 2 and 3 are graphs showing schematically examples of evolution of the traction effort F applied near to an end of the pre-stressed bar as a function of the two-way propagation time of the ultra-sonic waves during the preliminary calibration of the method according to the invention.
Figure 3:
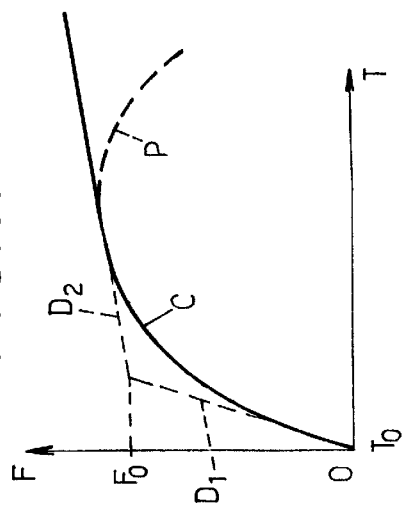

These recordings correspond to points of a curve of the traction effort F as a function of the two-way propagation time T, such as the curve represented in FIG. 2 or 3.

This curve C typically has:

an initial portion which approximately follows a straight line $D_1$ of slope $k_a$ which is relatively large and is representative of the elongation of the part of the bar 1 between the nut 3 and the ring 12, then an upper portion which, with the great values of the effort F, substantially follows a straight line $D_2$ of slope $k_L < k_a$, which is representative of the elongation of all the stressed part of the bar 1, whereby the length of this part is L=b+a where b is the length between the two anchorages 2, 3 and a is the length between the anchorage 3 and the ring 12 (FIG. 1).

As is known per se, the intersection of the straight lines $D_1$ and $D_2$ corresponds to an ordinate $F_0$ which represents the residual tension of the pre-stressed bar during calibration.

The micro-computer 8 is programmed to determine the straight lines $D_1$ and $D_2$ as well as their point of intersection. The micro-computer deduces therefrom a constant $F_0$ which is the traction effort F corresponding to this point of intersection, i.e. the value of the residual tension during calibration.

The micro-computer 8 also memorizes the value $T_0$ of the two-way propagation time T obtained during the calibration in the absence of application of the traction effort, i.e. for F=0.

The point having the co-ordinates ($T_0$, $F_0$) is a point of the curve linking the two-way propagation time to the residual tension in the pre-stressed bar, in the absence of the calibration system. As we know that this curve is linear, its equation takes the form:

$$F_1 = F_0 + k_b \cdot (T_1 - T_0) \qquad (1)$$

which enables the value of the residual tension $F_1$ to be deduced from the simple measurement of a two-way propagation time $T_1$.

In order to determine the slope coefficient $k_b$, during calibration, the micro-computer 8 uses the relationship:

$$1/k_b = (1/k_L) - (1/k_a) \qquad (2)$$

Owing to this, the coefficient $k_b$ correctly takes account of the behaviour of the stressed zone, of length b, of the bar 1.

In the example illustrated by FIG. 2, it is considered that the curve C consists essentially of two linear portions, connected by a rounded portion. The micro-computer 8 thus fits two straight lines $D_1$ and $D_2$ of slopes $k_a$ and $k_L$ on the lower and upper portions of the curve resulting from the measurements made during calibration, for example by a conventional least square fit method, and deduces therefrom the constant $F_0$ as well as the constant $k_b$ according to the relationship (2).

In order to further improve the precision of the calibration, the micro-computer 8 can be programmed to adjust a parabola P on the lower portion of the curve C. Indeed, it can be shown that, taking into account the threads engaging the pre-stressed bar 1, the lower portion of the curve C is parabolic rather than linear. FIG. 3 shows such an embodiment (exagerating the curving of the parabola P). The above-described calculations are carried out in the same way, using as the straight line $D_1$ the tangent at the point ($T_0$, 0) of the parabola determined. This straight line $D_1$ is an approximation of the points of the curve C which are closest to the origin ($T_0$, 0).

Once the calibration has been carried out once for all, when one subsequently wishes to check the value of residual tension $F_1$ of the pre-stressed bar 1, it is no longer necessary to equip the end 5 of this bar with the unit 11, but solely with the transducer 7 linked to the micro-computer 8.

The micro-computer 8 then simply causes the transducer 7 to emit an ultra-sonic wave, preferably as a pulse, at the end 5 of the pre-stressed bar. Then the transducer 7 senses the echoing ultra-sonic wave after reflection on the end 4 of the bar, and the micro-computer 8 measures the two-way propagation time $T_1$ of the ultra-sonic wave. On the basis of this two-way propagation time $T_1$, the micro-computer 8 deduces the value of the residual tension $F_1$ at the time of measurement by the formula (1).

It is known that the temperature of a material, such as the steel of the bar 1, has an effect upon the ultra-sound propagation speed in this material and thus upon the measured two-way propagation propagation time. Consequently, if the temperature of the bar is susceptible to variation, it is advantageous to provide automatic correction in the processing of the measurements by application of a formula of the type:

$$T_1 = T_m + \beta \cdot (\theta_m - \theta_i) \quad (3)$$

where $T_m$ is the two-way propagation time measured at the temperature $\theta_m$, $T_1$ is the corrected time used for the application of the formula (1), corresponding to a temperature $\theta_i$, for example the temperature during calibration, $\beta$ a pre-determined constant depending upon the material and its geometrical characteristics.

The temperature $\theta_i$ of the material of the bar is measured during calibration, then during subsequent measurements so that the correction (3) is applied. The measurement of temperature can be carried out by means of a sensor 20, such as a thermocouple, neighboring the ultra-sonic transducer 7 or integrated into it.

What is claimed is:

1. A method for measuring in situ a residual tension $F_1$ of a pre-stressed bar braced between two anchorages by determining a two-way propagation time $T_1$ of an ultrasonic wave between two longitudinal ends of the bar and by evaluating the residual tension $F_1$ by a formula of the form $F_1 = F_0 + k_b \cdot (T_1 - T_0)$, where $F_0$, $T_0$ and $k_b$ are constants determined during a preliminary calibration carried out without demounting the bar, whereby the preliminary calibration comprises the steps of:

subjecting the bar to different values of a traction effort F, applied in a zone situated outside of the interval between the two anchorages;

for each value of the applied traction effort F, measuring the two-way propagation time T of an ultra-sonic wave between the two longitudinal ends of the bar, to memorize points of a curve associating the traction effort F with the two-way propagation time T;

determining the constant $T_0$ as being the two-way propagation time T measured for a traction effort F=0;

identifying on initial portion of said curve, in the neighborhood of the traction effort value F=0, by a first straight line having a slope $k_a$;

identifying an upper portion of said curve by a second straight line having a slope $k_L$;

determining the constant $F_0$ as being the traction effort F corresponding to the point of intersection of said first and second straight lines; and determining the constant $k_b$ according to $1/k_b = (1/k_L) - (1/k_a)$.

2. A method according to claim 1, wherein the approximation of said curve in the neighborhood of the value of the traction effort F=0 by a first straight line having a slope $k_a$ comprises a fit of a parabola on a lower portion of the curve, and the determination of the first straight line as being a tangent of said parabola for the value of traction effort F=0.

3. A method according to claim 1, wherein the preliminary calibration comprises a measurement of the temperature of a material of the bar and a memorization of the temperature measured.

4. A method according to claim 3, wherein a measuring phase subsequent to the calibration comprises the steps of measuring the temperature of the material of the bar and the two-way propagation time of an ultra-sonic wave between the two longitudinal ends of the bar, and determining the time $T_1$ for the application of said formula by correcting the measured two-way propagation time as a function of the deviation between the temperatures measured during the preliminary calibration and the subsequent measuring phase.

* * * * *